United States Patent [19]

Lombardo et al.

[11] 4,325,483

[45] Apr. 20, 1982

[54] METHOD FOR DETECTING AND CONTROLLING FLOW RATES OF THE DROPLET FORMING STREAM OF AN ELECTROSTATIC PARTICLE SORTING APPARATUS

[75] Inventors: Igino Lombardo, Sharon; Donald E. Barry, Norwood; W. Peter Hansen, Middleboro, all of Mass.

[73] Assignee: Ortho Diagnostics, Inc., Raritan, N.J.

[21] Appl. No.: 68,231

[22] Filed: Aug. 20, 1979

[51] Int. Cl.³ .............................................. B07C 5/342
[52] U.S. Cl. .................................... 209/3.1; 209/579; 209/906; 250/222 PC; 346/75; 356/72; 361/226; 364/413
[58] Field of Search ................................. 209/3.1–3.3, 209/571, 579, 906, 127 R; 356/39, 72, 73, 335, 338; 250/222 R, 222 PC; 361/226; 364/413; 346/75

[56] References Cited

U.S. PATENT DOCUMENTS

| 3,380,584 | 4/1968 | Fulwyler | 209/3 |
|---|---|---|---|
| 3,710,933 | 1/1973 | Fulwyler et al. | 209/3 |
| 3,761,941 | 9/1973 | Robertson | 346/1 |
| 3,769,627 | 10/1973 | Stone | 346/75 |
| 3,826,364 | 7/1974 | Bonner et al. | 209/3.1 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 346/75 |
| 3,907,429 | 9/1975 | Kuhn et al. | 356/28 |
| 3,920,702 | 10/1975 | Corll | 356/72 |
| 3,941,479 | 3/1976 | Whitehead | 356/102 |
| 3,953,860 | 4/1976 | Fujimoto et al. | 346/75 |
| 3,963,606 | 6/1976 | Hogg | 209/3 |
| 3,982,251 | 9/1976 | Hochberg | 346/1 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/75 |
| 4,047,183 | 9/1977 | Taub | 346/1 |
| 4,063,252 | 12/1977 | Jensen et al. | 346/75 |
| 4,148,718 | 4/1979 | Fulwyler | 209/3.1 |

OTHER PUBLICATIONS

Buehner et al., "Two-Level Ink Jet Deflection Control System", IBM Technical Disclosure Bulletin, vol. 16, No. 10, 3-74.

"Laser Flow Microphotometry for Rapid Analysis and Sorting of Mammalian Cells", Mullaney, et al., Annals New York Academy of Sciences, vol. 267, pp. 176-190.

"Feedback for Synchronized Pressure Jet Using Optical Sensor", IBM Technical Disclosure Bulletin, vol. 16, No. 12, May 1974, pp. 3877-3878.

"Phase Detection on Ink Jet Droplets", IBM Technical Disclosure Bulletin, vol. 16, No. 3, Aug. 1973, p. 880.

*Primary Examiner*—Joseph J. Rolla
*Attorney, Agent, or Firm*—Audley A. Ciamporcero

[57] ABSTRACT

A novel method is disclosed for detecting and controlling the flow rate of a perturbed, droplet-forming stream in an electrostatic particle sorting apparatus. Detection apparatus is located at two points along the stream, at a first particle sensing point for sensing the presence of particles within a core portion of the stream, and at a second downstream point, preferably the stream breakpoint, for sensing light scatter and extinction characteristics which are proportional to the surface characteristics of the sheath portion of the stream. Changes in phase shift, pulse width, duty cycle, pulse area, or breakpoint location are detected by analyzing these sheath surface-related characteristics. An error signal is produced in response to such changes which drives an electromechanical fluid flow regulator to increase or decrease the fluid flow rate in a direction which tends to minimize the error signal. The flow rate is thus maintained at a reference flow rate setting.

43 Claims, 2 Drawing Figures

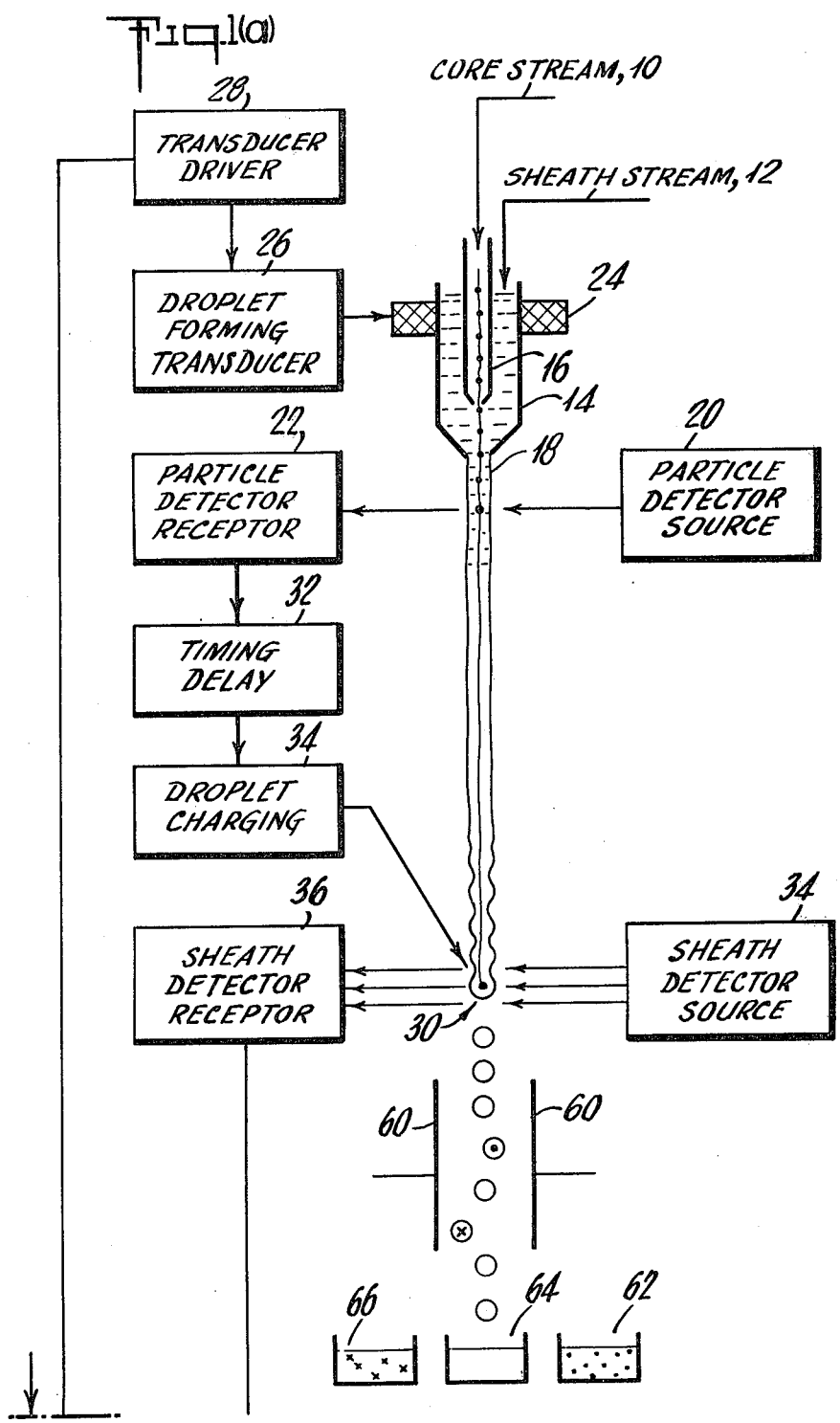

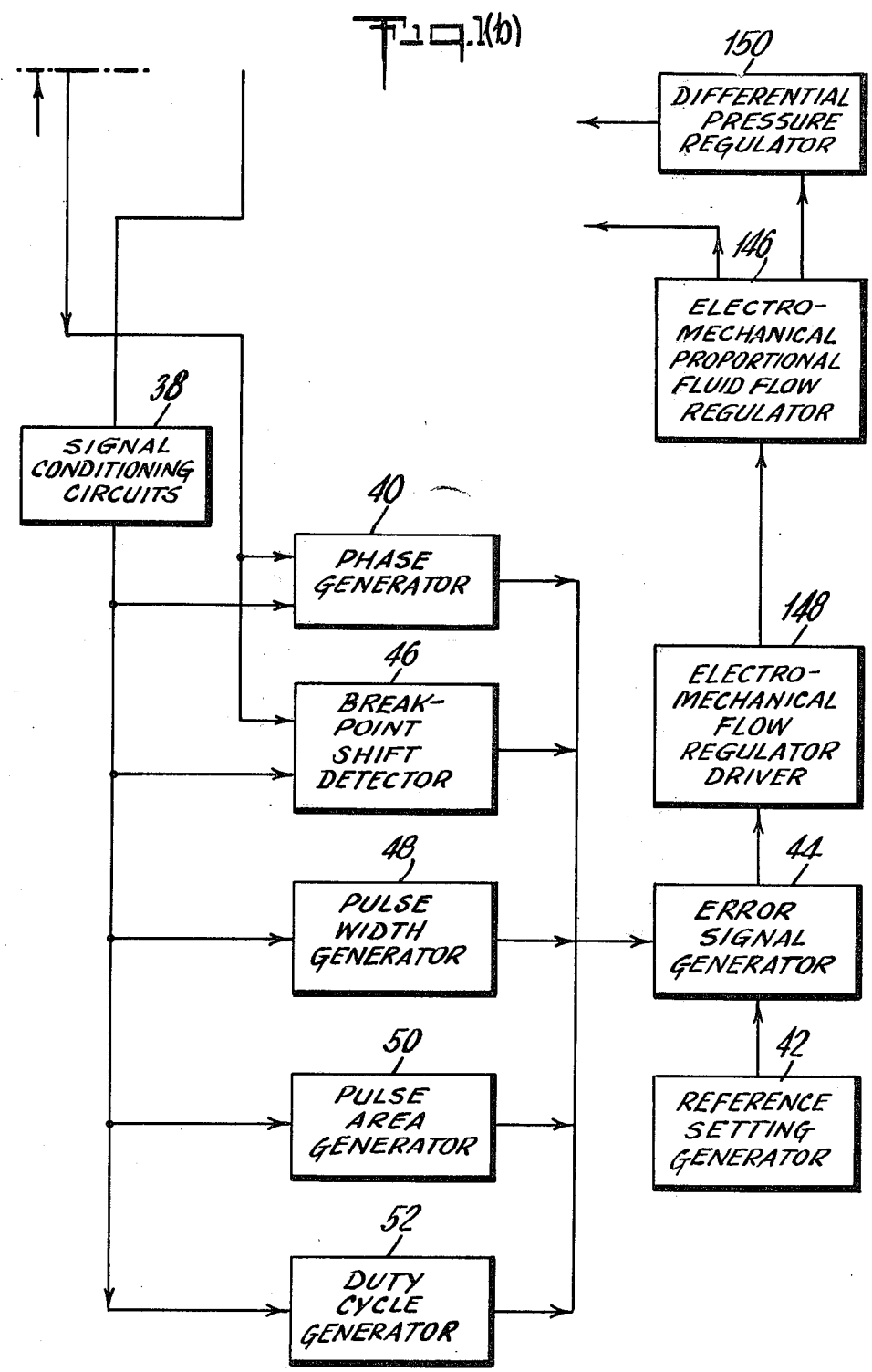

METHOD FOR DETECTING AND CONTROLLING FLOW RATES OF THE DROPLET FORMING STREAM OF AN ELECTROSTATIC PARTICLE SORTING APPARATUS

CROSS REFERENCE TO RELATED APPLICATIONS

The present application is related to the following applications, each of which is assigned to the assignee of the present application and are hereby incorporated by reference as if fully set forth herein: the invention of Igino Lombardo and W. Peter Hansen entitled, "Method And Apparatus For Positioning The Point Of Droplet Formation In The Jetting Fluid Of An Electrostatic Sorting Device", Ser. No. 68,113, filed Aug. 20, 1979; the invention of Igino Lombardo and Donald E. Barry entitled, "Automatic Relative Droplet Charging Time Delay System For An Electrostatic Particle Sorting System Using A Relatively Moveable Stream Surface Sensing System", Ser. No. 68,259, filed Aug. 20, 1979; the invention of Igino Lombardo and Donald E. Barry entitled, "Method For Automatically Setting The Correct Phase Of The Charge Pulses In An Electrostatic Flow Sorter", Ser. No. 68,234, filed Aug. 20, 1979; the invention of Donald E. Barry and Igino Lombardo entitled, "A Method For Measuring The Velocity Of A Perturbed Jetting Fluid In An Electrostatic Particle Sorting System", Ser. No. 68,235, filed Aug. 20, 1979; and the invention of Richard A Dussault and Igino Lombardo entitled, "A Servo System To Control The Spatial Position Of Droplet Formation Of A Fluid Jet In A Cell Storing Apparatus", Ser. No. 68,112, filed Aug. 20, 1979.

As to Ser. No. 68,259, please see generally pages 15–22; as to Ser. No. 68,113, see generally pages 15–24; as to Ser. No. 68,234, see generally pages 15–21; as to Ser. No. 68,235, see generally pages 15–22; and as to Ser. No. 68,112, see generally pages 15–27.

BACKGROUND OF THE INVENTION

The present invention relates generally to the field of electrostatic flow sorters, and more particularly to those sorters which are adapted to sense the presence and/or character of particles in a laminar flow stream and to selectively sort those particles by breaking that stream into a number of discrete droplets, and soring those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, an electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interest arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Microphotometry For Rapid Analysis And Sorting Of Mammalian Cells", Mullaney, et al, Annals New York Academy Of Sciences, Vol. 267, pages 176–190 (see in particular, pages 180 and FIGS. 3 and 4).

Such particle sorters are also disclosed in U.S. Pat. No. 3,710,933 (Fulwyler, et al) and 3,380,584 (Fulwyler) and 4,148,718 (Fulwyler). In these patents, sorting is accomplished in accordance with a selected parameter which may be size, volume, presence of radioactivity, color, florescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14–49.

As described particularly in U.S. Pat. No. 3,710,933, (Fulwyler, et al), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al to be in the order of 1400 microseconds) can be estimated so that an appropriate droplet charging generator will operate in combination with a pulse height analyzer and cell separation logic to charge the selected cell containing dropleets for subsequent electrostatic sorting.

A number of factors affect the ability of a given apparatus to selectively sort one or more types of target cells from a continuous cell stream. Even assuming that the detection equipment for identifying each cell to be sorted is 100% accurate, differences in flow rate, temperature, fluid viscosity, and transducer performance can affect the time delay or location of the desired target-cell-containing droplets at the breakpoint, which is the point at which a charge pulse must be administered to insure that the target cell will be subsequently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are adjusted to provide the necessary time delay to allow for travel time of the particle from the point of particle scatter detection to the point where the stream breaks into drops. Bonner states:

"With the present arrangement the delay time between observation of a particle and its capture by a separating droplet is predictable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22-32.

As further explained in the Bonner, et al disclosure, the duration as well as the time of application of the charging pulse is critical to the separation of at least the droplet containing the target particle to be sorted. After describing a preferred charging pulse which will charge at least three drops, Bonner, et al states:

"Obviously, if instrument tolerances, variations, drift and like permitted, then a drop charging time sufficient to charge only two successive drops, or a single drop, could be employed." U.S. Pat. No. 3,826,364, Col. 8, lines 2-6.

As also pointed out by Bonner, et al, a drop breaking from a given flow stream carries with it a charge which is proportional to the potential between the droplet stream and the surrounding electrodes or charging surfaces at the time the drop separates from the stream. If the drop breaks off from the jet stream during the transition time from the drop charge pulse, either during the leading or trailing edge of that pulse, some intermediate value between zero and the desired full charge may be imparted to the target droplet. In the Bonner, et al apparatus, on/off transitions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the defleted drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet forming aperture to the point of break off. Hogg proposes the uses of a movable scale in place of the ground glass of prior art projection microscopes, this scale being linked to a potentiometer of an RC oscillator to thereby control the osciallator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23-36. Accordingly, Hogg represents a more automated version of the stroboscopic projection microscopic techniques discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establishing uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wherein a light source and photocell located downstream from the breakpoint of a perturbed stream is used to sense the passage of discrete droplets and to time delayed charges subsequently applied thereto. Stone states:

"Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore, that the charging process must be carefully synchronized with the timing of the drop break off. This involves the use of complex phasing control sensors and loops. This in turn, increases the cost of the equipment.

It is an object of this invention to provide an ink drop charging system which does not depend upon the synchronization of the charging with the break off time.

It is another object of this invention to produce an ink drop charging system, which charges drops after they break off from the ink jet stream." U.S. Pat. No. 3,769,627 (Stone), Col. 1, lines 18–35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

"The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53–68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phases of fundamental and harmonic frequencies. Taub states:

"The light passing through the slit 44 is influenced by the wave passing a given point on the perimeter of the jet, and accordingly is a representation of the frequency components of the jet at this particular point, as well as being indicative of the shape of a given droplet when it breaks-off downstream. it is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100A centered in the laser wavelength, is used so measurements may be made in room light. The light passed by the filter 48 is then transmitted to a photomultiplier tube 50 which measures the intensity of the light. Therefore, the output voltage of the photomulitplier tube 50 is proportional to the diameter of the jet blocking the slit, which is to say, to the local diameter of the jet at the point being probed . . . It is to be appreciated that the signal output . . . may be applied to analyzingmeans 80 by other timing means such as a stepping motor, or alternatively may be applied concurrently to inputs of devices 82, 84 and 86, rather than in the time sequence described." U.S. Pat. No. 4,047,183. See Col. 6, lines 27–68, Col. 7, lines 1–26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877–78, entitled "Feedback For Synchronized Pressure Jet Using Optical Sensor"; and IBM Technical Disclosure Bulletin, Vol. 16, No. 3, August 1973, Page 880, entitled "Phase Detection On Ink Jet Droplets".

For other disclosures relating to various ink jet printing synchronization systems, please refer to U.S. Pat. No. 4,025,926 (Fujimoto, et al) entitled, "Phase Synchronization For Ink Jet System Printer"; U.S. Pat. No. 4,045,770 (Arnold, et al) entitled, "Method and Apparatus For Adjusting The Velocity Of Ink Drops In An Ink Jet Printer"; U.S. Pat. No. 3,953,860 (Fujimoto, et al) entitled, "Charge Amplitude Detection For Ink Jet System printer"; U.S. Pat. No. 3,761,941 (Robertson) entitled, "Phase Control For A Drop Generating and Charging System"; U.S. Pat. No. 3,836,912 (Ghougasian, et al) entitled, "Drop Charge Sensing Apparatus For Ink Jet Printing System"; U.S. Pat. No. 3,982,251 (Hochberg) entitled, "Method and Apparatus For Recording Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles In A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention provides a novel method for monitoring and controlling the flow rate of a droplet forming stream in an electrostatic particle (flow) sorting system. This system preferably comprises flow means for establishing the flow of a continuous particle containing stream comprising at least particle containing core stream portion and a surrounding sheath stream portion. In the preferred embodiment, this stream has a particle sensing point defined therealong at which an optical detection means for detecting and distinguishing particles is located. The stream is caused to form discrete droplets under the influence of a perturbation means for perturbing the stream with at least a preselected frequency and amplitude. A breakpoint is thus formed at which the stream breaks into a series of discrete droplets. A droplet charging means is provided for relatively charging selected ones of said droplets as they are formed at said breakpoint, and synchronization means is provided for timing that relative charging such that the selected droplets contain at least the selected particles which were previously detected at the particle sensing point by said optical detection means.

In accordance with the present invention, the synchronization means comprises a sheath sensing means for sensing, (at a point subsequent to said perturbation), the light scatter and extinction characteristics of the sheath portion of the stream. These characteristics are believed to be proportionally related to the surface character of the stream. Surface character analysis means are provided for analyzing the signal produced by the sheath sensing means to determine the phase, pulse width, duty cycle, and/or breakpoint position of the stream. These values are then compared with appropriate reference values. If the determined and reference values differ, an error signal is produced which acts through an electromechanical proportional fluid flow regulator to increase or decrease the fluid flow rate in a direction which will tend to minimize the error signal. Control of the stream flow rate at reference flow rate settings is therefore automatically effected.

In the preferred embodiment, the sheath sensing means comprises a radiant energy source, such as a laser or other light source, which is focused to pass through at least the sheath stream portion of the flow stream. The sheath stream and radiant energy source are selected so that the sheath stream portion is essentially translucent with respect to the radiant energy source, such that significant energy (light) scattering occurs as that energy is directed through the sheath stream portion of the flow stream. A light/energy detector is positioned to monitor energy which is not scattered by the flow stream, thereby producing a signal which is proportional to the surface characteristics of the flow stream. p In the preferred embodiment, the particle-containing core stream portion, which is surrounded by the sheath stream portion of the flow stream, contains particles which are to be sensed by an optical detection means, which may also comprise a radiant energy source, such as a laser, which will induce light scatter, absorption, and/or florescence of at least a portion of the core stream.

Accordingly, a primary object of the present invention is the provision of a novel method and apparatus for detecting and controlling the flow rate of the perturbed flow stream of an electrostatic flow sorting apparatus. This and other objects of the present invention will become apparent following more detailed description.

BRIEF DESCRIPTION OF THE DRAWINGS

FIG. 1(*a*) and 1(*b*) are a diagrammatic hybrid block drawing of the system of the present invention.

DETAILED DESCRIPTION OF THE DRAWINGS

Although specific forms of the invention have been selected for illustration in the drawings, and the following description is drawn in specific terms for the purpose of describing these forms of the invention, this description is not intended to limit the scope of the invention which is defined in the appended claims.

As seen in particular in FIG. 1, the system of the present invention is intended for use with an electrostatic particle (flow) sorting system. As is typical of such systems, a flow means is provided for establishing the flow of a continuous particle containing stream, comprising at least a particle-containing core stream portion and a surrounding sheath stream portion. Referring to FIG. 1, the particle containing core stream 10 and surrounding sheath stream 12 are shown combining within core chamber 14. The core stream 10 is injected into the sheath stream 12 by sample injection tube 16. In accordance with the preferred embodiment of the present invention, the resulting laminar stream 18 then passes by a particle detection point at which incident radiant energy from a particle detector source 20, such as a helium-neon laser, facilitates detection of particular particles to be sorted by one or more particle detector receptor(s) 22. This detector(s) may be scattered or florescent light detectors or other detector(s) known to this art for this purpose.

A perturbation means for perturbing the stream at least at a preselected frequency and amplitude is provided to cause the laminar stream 18 to form a breakpoint 30, at which the stream becomes a series of discrete droplets. The perturbation means comprises a transducer driver 28, a droplet forming transducer 26, and a transducer orifice 24 through which the laminar stream 18 passes. A droplet charging means is also provided for relatively charging selected ones of said droplets as they are formed at the breakpoint 30. The droplet charging means comprises a time delay circuit 32 and droplet charging means 24 for inducing a charge upon a preselected droplet at the droplet breakpoint.

Since breakpoint occurrance in a perturbed laminar flow stream is dependent upon the flow rate of that stream, one of the objects of the present invention is to control the flow rate of that stream so that a preselected timing delay will cause the charging of the particular particle-containing droplet. Accordingly, a synchronization means for timing the relative charging of droplets at the breakpoint is provided which further comprises sheath sensing means for sensing the light scatter and extinction character of the stream at a point therealong subsequent to said perturbation. Since the charge of a particular droplet is fixed at the breakpoint, the sheath sensing means should preferably be located precisely at the droplet breakpoint. Alternatively, the sheath detector means may be located adjacent to the breakpoint, but not by such a distance as to permit the introduction of substantial error due to flow rate variations which may occur between the location of the sheath sensing means and the breakpoint.

In accordance with the preferred embodiment of the present invention, the sheath sensing means comprises a sheath detector source 34 which may be a radiant energy source with respect to which the sheath fluid is translucent. While an separate helium-neon laser source is the preferred radiant energy source for this purpose, it is also contemplated that a portion of the radiant energy emitted by the particular detector source may be transmitted to this location for this purpose. Alternatively, other radiant energy sources, such as conventional light sources, could be used for this purpose. The sheath detector source also comprises conventional optics, such as lenses, etc. which are sufficient to create an energy beam focused on the laminar flow stream. The beam width should be approximately equal to or slightly greater than the greatest diameter of the stream at this point. A sheath detector receptor 36 is axially aligned on the opposite side of the stream to receive the incident light which is not scattered by the translucent sheath stream portion. It is anticipated that the core stream 10 which forms a portion of the laminar stream 18 may, in fact, be opaque with respect to the sheath detector source energy and therefore may absorb a small portion of that energy. In view of the geometry of the laminar stream, however, and the relatively small proportion of the stream which is comprised of core stream material, the opacity of the core's stream exerts a negligible effect upon the amount of energy detected by the sheath detector receptor 36 by comparison to the light scattering effects of the translucent sheath stream portion of the laminar flow stream 18. Due to the different geometric configuration of the laminar flow stream, the sheath detector receptor will produce a signal which, when subjected to conventional signal conditioning circuits 38, such as amplification and filtering circuits, will produce a waveform which is characteristic of the particular surface geometry of the laminar stream at the point of sheath stream detection. This signal may then be transmitted in combination with a reference signal received from the transducer driver 28 to one or more surface character analysis means for producing an output signal which is at least selectively responsive to said sheath sensing means. In the preferred embodiment, the signal from the sheath sensing means may be analyzed for phase shift, break point shift, pulse width detection, pulse area detection and/or duty cycle detection. In accordance with the preferred embodiment of the present invention, only one of these characteristics of the output of the sheath detector receptor 36 need be analyzed and compared with a flow rate reference setting 42 by an error signal generator 44 which acts to regulate the flow of both the core and sheath streams.

Referring to FIG. 1, the output of the signal conditioning circuits 38 may be fed to a phase generator 40, which also receives the output of the transducer driver 28. Since the frequency of the sheath detector signal may be assumed to be the same as that imparted to the laminar stream at orifice 24 by the transducer driver 28, the output of the transducer driver may be utilized as a frequency synchronous clock. Accordingly, the output from the transducer drier may be used to trigger the phase generator at a given point in each sheath detector receptor output cycle. In this embodiment, the output from the phase generator 40 will be compared to a phase generator reference setting which is omitted by the reference setting generator 42 for comparison by the error signal generator 44. The output of the error signal generator is proportional to the difference between the phase generator 40 and the reference setting generator 42, to thereby act through an electromechanical flow regulator driver 146 and electromechanical proportional fluid flow regulator 148 to affect the flow rates of the sheath stream 12 and indirectly the core stream 10. Since corresponding sheath stream flow rate variations would otherwise inversely affect the flow rate of the core stream, a differential pressure regulator 150 is provided to proportionally vary the flow rate of the core stream in response to adjustments in the sheath stream flow. In this manner, the device of the present invention automatically compensates for factors, such as flow stream viscosity, surface tension, and temperature, which otherwise might affect the flow rate of the laminar stream, and thereby prevent the droplet charging circuit 34 from inducing the required charge on those droplets containing particles to be sorted from the stream.

In addition to detecting for shifts in phase of the sheath detector receptor output, it is also possible to detect flow rate variations by detecting shifts in breakpoint, pulse width, pulse area, or duty cycle of the output of the sheath detector receptor. Accordingly, a breakpoint current-waveform generator (i.e. shift detector) 46, a pulse width generator 48, a pulse area generator 50 or a duty cycle generator 52 may be provided and compared with appropriate reference settings to determine whether a variation in flow rate, as represented by a compared difference, has occurred. For example, the detection of a spatial shift in the droplet formation breakpoint by the detection of changes in the scatter or extinction of light by the sheath detector receptor 36 is possible when the sheath detector source 34 is focused on the breakpoint. The detection is carried out by chopping the sheath detector receptor output 36 utilizing a synchronizing signal occurring at a specific time in the droplet formation cycle, so as to observe changes in the breakpoint position at a constant point in time. In accordance with the preferred embodiment, the synchronizing signal utilized for this purpose is that of the transducer driver 28. As with the above-mentioned phase generator, the error signal generator 44 compares the output of the breakpoint—current waveform generator 46 with an appropriate breakpoint reference setting from the reference setting generator 42, which acts as described above to alter the flow rate of the laminar flow stream 18.

The detection of pulse widths of the waveform obtained when a light source is focused on any portion of the droplet stream and the scatter or extinction of light is electrically measured with the sheath detector receptor, is also proportional to changes in flow rate. Similarly, the detection of the duty cycle of the waveform and the detection of the pulse area of the waveform are similarly flow rate dependent.

One of ordinary skill in the art will recognize that each of the generators 40, 46, 48 are readily available to one of ordinary skill in this art. For example, conventional counting and timing circuits may be used to derive the pulse widths and duty cycles of a given waveform, while pulse area may be conveniently derived through conventional integration circuitry. Similarly, as mentioned above, choppers may be used as triggered by the output from the transducer driver to produce phase synchronous values for both the phase generator and breakpoint-current waveform generator. In accordance with the preferred embodiment of the present invention, a breakpoing-current waveform generator may utilize the analysis techniques of Richard A. Dussault and Igino Lombardo as described in the above-referenced related patent application entitled, "A Servo System To Control the Spatial Position Of Droplet Formation Of A Fluid Jet In A Cell Sorting Apparatus", which application has been incorporated herein by reference.

As seen from the above description, the present invention provides a simple and extremely efficient way of insuring that a given timing delay will enable droplet charging of a particle which has been previously detected by a particle detection means located substantially upstream from the breakpoint. Since the present apparatus is capable of sensing and adjusting for even slight shifts in phase, the present apparatus insures that a particle sensed upstream will be contained in a droplet which is subjected to a sorting charge. The charged droplet may subsequently be deflected by deflection plates 60 for collection in appropriate sample collection vessels 62, 64, and 66. Accordingly, slight variations in temperature, viscosity and other factors which would normally adversely affect the performance of a sorting apparatus of this kind are eliminated as causes of flow rate variations. By recognizing that droplet volume, droplet spacing, droplet formation distance from the nozzle (droplet breakpoint), and phase shift between applied disturbance and the forming droplets, are flow rate dependent, a number of alternate means have been described for producing an extremely simple, yet efficient flow rate invariant droplet sorting system.

In accordance with an alternate embodiment of the present invention, a single radiant energy source may be utilized as both the particle detector souce 20 and the sheath detector source 34. For example, it is anticipated that a single helium neon laser may be utilized as those sources, a portion of the energy, as for example, the scattered energy omitted from that laser, being collected and directed for use as the sheath detector source 34. In this manner, the expense of providing an additional laser source for sensing the surface character of the laminar flow stream is substantially diminished.

In accordance with the preferred embodiment of the present invention, the sheath sensing means for sensing the surface character of the laminar flow stream at a sheath sensing point therealong subsequent to said perturbation, and for producing a surface character output signal which is proportional thereto, may comprise a suitable radiant energy source, such as a light emitting diode, a conventional light source of white light, or a laser or laser diode. Suitable optics should be provided for the purpose of focusing the radiant energy upon the stream. A lens assembly comprising two cylindrical lenses has been found to be suitable for this purpose, each of these lenses having their axis oriented perpendicular to the axis of incident light, as well as perpendicular with respect to each other. It has been found suitable to utilize a front cylindrical lens having a focal length of approximately 6 mm and a back lens having a focal length of approximately 11 cm. The preferred sheath detector receptor is a photodiode, but may also be a photomultiplier. Of the above-identified lenses, the front lens tends to focus the radiant energy upon the stream, while the back lens focuses incident energy towards the diode. It has been found suitable to use a conventional FC200 Ortho Instruments' lens assembly for this purpose. This lens assembly may, for example, be placed approximately ¼ inch from the flow stream, and the photodiode placed approximately 1 inch on the opposite side of the stream past the point of focus of the lens assembly for the purpose of permitting the photodiode to pick up a substantial portion of the light neither scattered nor extinguished by the stream, but not so much light as to permit detector saturation.

It will be understood that various changes in the details, materials and arragements of parts which have been described and illustrated in order to explain the nature of this invention may be made by those skilled in the art within the principle and scope of the invention as expressed in the following claims. As used herein, "perturbed" or "perturbation" is meant to include not only mechanical/vibratory methods for creating dicontinuities in the stream, but also discontinuities which are induced by other means such as alteration of stream surface tension, for example, by electrical, thermal, or optical means. LIkewise, periodic or aperiodic perturbations are meant to be included.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention as described and claimed herein.

What is claimed is:

1. An electrostatic particle sorting system, comprising:
   (a) flow means for establishing the flow of a continuous particle containing stream comprising at least a particle containing core stream portion and a surrounding sheath stream portion, said stream having a particle sensing point defined therealong;
   (b) optical detection means for optically detecting said particles at least at said particle sensing point;
   (c) perturbation means for perturbing said stream with at least a preselected frequency and amplitude to cause said stream to form a breakpoint at which said stream becomes a series of discrete droplets;
   (d) droplet charging means for relatively charging selected ones of said droplets as they are formed at said breakpoint; and
   (e) synchronization means for timing said relative charging such that said selected droplets contain at least selected particles detected by said optical detection means; said synchronization means comprising:
      (i) sheath sensing means for sensing at least the light scatter of said sheath stream portion at a sheath sensing point therealong subsequent to said perturbation and for producing a surface character output signal which is proportional thereto;
      (ii) surface character analysis means for producing an output signal which is at least selectively responsive to said sheath sensing means;
      (iii) flow rate adjustment means responsive to said surface character analysis means for establishing and maintaining a preselected flow rate of said stream.

2. The invention of claim 1 wherein said system further comprises a radiant energy source, said source providing energy for said optical detection means and for said sheath sensing means.

3. The invention of claim 1 wherein surface character analysis means comprises phase shift detection means for sensing shifts in phase of said surface character output signal.

4. The invention of claim 3 wherein said phase shift detection means comprises a phase reference generator, second means for generating a signal representative of actual phase conditions, and error signal generation means for comparing signals generated by said phase reference generator and said second means for generating to produce an error signal proportional to the differences therebetween.

5. The invention of claim 4 wherein said second means for generating comprises means for sensing at periodic intervals the value of at least a portion of said surface character output.

6. The invention of claim 5 wherein said second means for generating comprises interval establishment means for sensing said frequency of said perturbation means to thereby establish said intervals.

7. The invention of claim 1 wherein said surface character analysis means comprises breakpoint shift detection means for sensing shifts in the position of said breakpoint.

8. The invention of claim 7 wherein said breakpoint shift detection means comprises a breakpoint waveform generator, a second means for generating a signal representative of actual phase conditions, and an error signal generation means for comparing said breakpoint waveform and the other waveform from said second means to produce an error signal proportional to the direction of shift of said breakpoint from said sheath sensing point.

9. The invention of claim 8 wherein said second means comprises phase synchronization means for sensing said current waveform in a preselected phase.

10. The invention of claim 9 wherein said second means comprises means for sensing said frequency of said perturbation means to establish said phase.

11. The invention of claim 1 wherein said surface character analysis means comprises pulse width detection means for detecting the pulse width of said surface character output signal.

12. The invention of claim 11 wherein said pulse width detection means comprises a pulse width generator, a pulse width reference setting generator, and an error signal generator for comparing the outputs thereof and for producing an error signal in proportional response thereto.

13. The invention of claim 1 wherein said surface character analysis means further comprises a pulse area detection means for detecting the pulse area of said surface character output signal.

14. The invention of claim 13 wherein said pulse area detection means further comprises a pulse area generator, a pulse area reference setting generator, and an error signal generator means for comparing the output signals thereof and for producing a proportional error signal in response thereto.

15. The invention of claim 1 wherein said surface character analysis means further comprises a duty cycle detection means for detecting the duty cycle length of said surface character output signal.

16. The invention of claim 15 wherein said duty cycle detection means comprises a duty cycle generator, a duty cycle reference setting generator, and an error signal generator means for comparing the outputs thereof and for producing a proportional error signal in response thereto.

17. The invention of claim 1 wherein said sheath sensing means comprises a radiant energy source with respect to which the sheath stream portion is essentially translucent, and a radiant energy receptor for measuring at least the scatter of said radiant energy by said sheath stream portion and for producing an output signal proportional thereto.

18. The invention of claim 17 wherein said radiant energy source is a source of light energy.

19. The invention of claim 18 wherein said source of light energy is a helium neon laser.

20. The invention of claim 1 wherein said flow rate adjustment means comprises an electromechanical flow regulator driver, and an electromechanical proportional fluid flow regulator for at least altering the fluid flow of said sheath stream portion of said particle containing stream.

21. The invention of claim 20 wherein said flow rate adjustment means further comprises a differential pressure regulator for proportionally regulating the flow of said core stream portion with respect to variations in the flow of said sheath stream portion.

22. A method of electrostatically sorting particles comprising:
  (a) establishing a flow of a continuous particle containing stream having at least a particle containing core stream portion and a surrounding sheath stream portion, said stream having a particle sensing point defined therealong;
  (b) optically detecting said particles at least at said particle sensing point;
  (c) perturbing said stream with at least a preselected frequency and amplitude to cause said stream to form a breakpoint at which said stream becomes a series of discrete droplets;
  (d) relatively charging said ones of said droplets as they are formed at said breakpoint; and
  (e) synchronizing said relative charging such that said selected droplets contain at least selected particles detected by said optical detection step; said synchronizing step comprising the steps of:
    (i) sensing at least the light scatter characteristics of said sheath stream portion at a sheath sensing point therealong subsequent to the point of said perturbation for producing a surface character output signal which is proportional thereto;
    (ii) analyzing said surface character output signal to produce an analyzed output signal which is at least selectively responsive to said sheath sensing means; and
    (iii) adjusting the flow of at least a portion of said continuous particle containing stream at least in response to said analyzed output signal.

23. The invention of claim 22 wherein a single source of radiant energy is utilized as a radiant energy source for optically detecting said particles at least at said particle sensing point and as a radiant energy source for sensing the light scatter and extinction character of said sheath stream portion.

24. The invention of claim 22 wherein said step of adjusting said flow rate comprises the step of proportionally regulating the flow of said core stream portion with respect to said sheath stream portion.

25. The method of claim 22 wherein said step of analyzing said surface character output signal comprises the step of detecting shifts in phase in said surface character output signal.

26. The invention of claim 25 wherein the step of detecting the phase shift of said surface character output signal comprises the steps of producing a phase reference signal, generating a second signal representative of actual phase conditions, and comparing said reference signal and said second signal for producing an error signal proportional to the differences therebetween.

27. The invention of claim 26 wherein said step of producing said second signal comprises the step of sensing at periodic intervals the value of at least a portion of said surface character output signal.

28. The invention of claim 27 wherein said second signal detection step comprises the step of establishing said intervals by sensing said frequency caused by said perturbation step.

29. The invention of claim 22 wherein said surface character analysis step comprises the step of detecting shifts in the relative position of the breakpoint of said particle containing flow stream.

30. The invention of claim 29 wherein said step of detecting shifts in said breakpoint comprises the steps of generating a breakpoint waveform, generating a second signal representative of actual phase conditions, and comparing the breakpoint waveform and said second signal to produce an error signal proportional to the direction of shift of said breakpoint from said sheath sensing point.

31. The invention of claim 30 wherein said step of generating said second waveform signal comprises the step of synchronizing the phase of said waveform to produce said second signal in a preselected phase.

32. The invention of claim 31 wherein said step of generating said second waveform signal comprises the step of sensing the frequency of said perturbing to establish said preselected phase.

33. The invention of claim 22 wherein said step of analyzing said surface character comprises the steps of detecting the pulse width of said surface character output signal.

34. The invention of claim 33 wherein said step of detecting the pulse width comprises the steps of generating a pulse width signal, generating a pulse width reference setting signal, and comparing the outputs thereof for producing an error signal in proportional response thereto.

35. The invention of claim 22 wherein said step of analyzing the surface character further comprises the steps of detecting the pulse area of said surface character output signal.

36. The invention of claim 35 wherein said step of detecting said pulse area further comprises the steps of generating a pulse area signal, generating a pulse area reference setting signal, and comparing these said signals for producing a proportional error signal response thereto.

37. The invention of claim 22 wherein said step of analyzing said surface character further comprises the step of detecting the duty cycle length of said surface character output signal.

38. The invention of claim 37 wherein said step of detecting said duty cycle length comprises the steps of generating a duty cycle signal, generating a duty cycle reference setting signal, and comparing these said signals for producing a proportional error signal in response thereto.

39. The invention of claim 22 wherein said step of sensing said sheath comprises the steps of illuminating said sheath with a radiant energy source with respect to which the sheath stream is essentially translucent, and measuring at least the scatter of said radiant energy produced by said sheath stream portion to produce an output signal proportional thereto.

40. The invention of claim 39 wherein said step of illuminating said sheath stream with a radiant energy source comprises the step of illuminating said stream with a source of light energy.

41. The invention of claim 40 wherein said step of illuminating said sheath stream portion with light energy comprises the step of illuminating said sheath stream portion with a helium-neon laser.

42. an electrostatic particle sorting system, comprising:
(a) flow means for establishing the flow of a continuous particle containing stream comprising at least a particle containing core stream portion and a surrounding sheath stream portion, said stream having a particle sensing point defined therealong;
(b) detection means for detecting said particles at least at said particle sensing point;
(c) perturbation means for perturbing said stream with at least a preselected frequency and amplitude to cause said stream to form a breakpoint at which said stream becomes a series of discrete droplets;
(d) droplet charging means for relatively charging selected ones of said droplets as they are formed at said breakpoint; and
(e) synchronization means for timing said relative charging such that said selected droplets contain at least selected particles detected by said detection means; said synchronization means comprising:
  (i) sheath sensing means for sensing at least the light scatter of said sheath stream portion at a sheath sensing point therealong subsequent to said perturbation and for producing a surface character output signal which is proportional thereto;
  (ii) surface character analysis means for producing an output signal which is at least selectively responsive to said sheath sensing means;
  (iii) flow rate adjustment means responsive to said surface character analysis means for establishing and maintaining a preselected flow rate of said stream.

43. A method of electrostatically sorting particles comprising:
(a) establishing a flow of a continuous particle containing stream having at least a particle containing core stream portion and a surrounding sheath stream portion, said stream having a particle sensing point defined therealong;
(b) detecting said particles at least at said particle sensing point;
(c) perturbing said stream with at least a preselected frequency and amplitude to cause said stream to form a breakpoint at which said stream becomes a series of discrete droplets;
(d) relatively charging said ones of said droplets as they are formed at said breakpoint; and
(e) synchronizing said relative charging such that said selected droplets contain at least selected particles detected by said detection step; said synchronizing step comprising the steps of:

(i) sensing at least the light scatter characteristics of said sheath stream portion at a sheath sensing point therealong subsequent to the point of said perturbation for producing a surface character output signal which is proportional thereto;

(ii) analyzing said surface character output signal to produce an analyzed output signal which is at least selectively responsive to said sheath sensing means; and (iii) adjusting the flow of at least a portion of said continuous particle containing stream at least in response to said analyzed output signal.

* * * * *